(12) United States Patent
Schafer

(10) Patent No.: US 11,060,306 B2
(45) Date of Patent: Jul. 13, 2021

(54) ENGINEERED HARDWOOD FLOORING AND MANUFACTURE THEREOF

(71) Applicant: Schafer Hardwood Flooring Company, Tecumseh, MI (US)

(72) Inventor: Scott F. Schafer, Onsted, MI (US)

(73) Assignee: Schafer Hardwood Flooring Company, Tecumseh, MI (US)

(*) Notice: Subject to any disclaimer, the term of this patent is extended or adjusted under 35 U.S.C. 154(b) by 0 days.

(21) Appl. No.: 15/814,463

(22) Filed: Nov. 16, 2017

(65) Prior Publication Data

US 2018/0135312 A1 May 17, 2018

Related U.S. Application Data

(60) Provisional application No. 62/423,506, filed on Nov. 17, 2016.

(51) Int. Cl.
*F26B 7/00* (2006.01)
*E04F 15/04* (2006.01)
(Continued)

(52) U.S. Cl.
CPC .......... *E04F 15/045* (2013.01); *A61L 2/0023* (2013.01); *B27K 5/001* (2013.01);
(Continued)

(58) Field of Classification Search
CPC . B27K 5/001; B27M 1/08; B32B 7/12; B32B 21/13; B32B 2250/03;
(Continued)

(56) References Cited

U.S. PATENT DOCUMENTS 2,556,686 A * 6/1951 Elmendorf ................ F26B 7/00
34/380
4,182,048 A 1/1980 Wolfe et al.
(Continued)

FOREIGN PATENT DOCUMENTS

CN 101596730 A 12/2009
CN 101623887 A 1/2010
(Continued)

OTHER PUBLICATIONS

11th International IUFRO Wood Drying Conference "Recent Advances in the Field of Wood Drying" Skelleftea Sweden, Jan. 18-22, 2010, Editors: Tom Morén Lena, Antti and Margot Sehlstedt-Persson, LTU Skellefteå, pp. 1-24.

*Primary Examiner* — Brian E Glessner
*Assistant Examiner* — James J Buckle, Jr.
(74) *Attorney, Agent, or Firm* — Michael T. Fluhler

(57) ABSTRACT

Methods and articles of manufacture relating to engineered hardwood flooring are provided. Engineered hardwood flooring is produced by drying a structural layer comprising a hardwood to a moisture content from about 0.1% to about 3%, whereupon a cell structure of the hardwood collapses. The dried structural layer is humidified to where the hardwood has an increased moisture content greater than about 3%. First and second outer layers are adhered to respective first and second sides of the structural layer to form an engineered product, the structural layer sandwiched by the first outer layer and the second outer layer.

20 Claims, 1 Drawing Sheet

(51) Int. Cl.
  *B27K 5/00* (2006.01)
  *B27M 1/08* (2006.01)
  *E04F 15/02* (2006.01)
  *A61L 2/00* (2006.01)
  *B32B 7/12* (2006.01)
  *B32B 21/13* (2006.01)
(52) U.S. Cl.
  CPC ......... *B27M 1/08* (2013.01); *E04F 15/02038* (2013.01); *B32B 7/12* (2013.01); *B32B 21/13* (2013.01); *B32B 2250/03* (2013.01); *B32B 2250/40* (2013.01); *E04F 2201/0107* (2013.01)
(58) Field of Classification Search
  CPC .... B32B 2250/40; B32B 21/00; E04F 15/045; E04F 15/02038; E04F 2201/0107; E04F 15/022; E04F 15/041; B27L 3/0214; F26B 2210/16
  USPC ....................................................... 52/592.1
  See application file for complete search history.

(56) References Cited

U.S. PATENT DOCUMENTS

| | | | |
|---|---|---|---|
| 4,227,965 A | 10/1980 | Luszczak | |
| 5,976,644 A | 11/1999 | Sanaee et al. | |
| 6,182,413 B1* | 2/2001 | Magnusson | B32B 3/266 |
| | | | 52/589.1 |

FOREIGN PATENT DOCUMENTS

| | | |
|---|---|---|
| CN | 101879736 A | 11/2010 |
| CN | 102241040 A | 11/2011 |
| CN | 103317567 A | 9/2013 |
| CN | 103788970 A | 5/2014 |
| WO | 2004067240 A1 | 8/2004 |

\* cited by examiner

ENGINEERED HARDWOOD FLOORING AND MANUFACTURE THEREOF

CROSS-REFERENCE TO RELATED APPLICATIONS

This application claims the benefit of U.S. Provisional Application No. 62/423,506, filed on Nov. 17, 2016. The entire disclosure of the above application is incorporated herein by reference.

FIELD

The present technology relates to manufactured wood products, including ways of preparing engineered hardwood flooring that minimize movement due to shrinkage or expansion.

INTRODUCTION

This section provides background information related to the present disclosure which is not necessarily prior art.

Preparation of various natural and engineered wood products often includes a drying process to remove moisture from green or cut timber. Green wood coming straight from a felled tree typically has far too high a moisture content to be commercially useful and may rot, warp, and/or split if not dried to a certain degree. Both hardwood and softwood can be dried until the moisture content is between 8% and 18%, for example. Drying can be a long process, or it can be sped up by use of various technologies such as a kiln. A variety of kiln technologies exist, including conventional, dehumidification, solar, vacuum, and radio frequency kilns. Kiln drying of wood holds a leading position within the various types of drying methods applied at an industrial scale, although other drying methods and hybrid methods are used.

Various modified drying processes, for example, can be employed to improve aspects of the resulting wood product. These drying processes include where high temperature drying is combined with a superheated steam environment, a combination of steam and heated air is used, an inert and dry gas is used, and one or more heated vegetable oils are used to remove moisture. Along with modification of the chemical structure and reduction of the hygroscopic nature of the treated and dried wood, high temperature treatment can also provide a plasticity increase where the wood becomes elastic at high temperatures, resistance to deformation is improved, warping tendency reduced, and the bending strength increased. Common goals of these various wood drying processes are to improve one or more properties of the resulting products, including shape and dimensional stability, resistance to delamination, weather resistance, bending strength, wear resistance, color, durability, etc.

Accordingly, minimizing dimensional movement due to shrinkage or expansion in natural and engineered wood products is desirable.

SUMMARY

The present technology includes systems, processes, articles of manufacture, and compositions that relate to preparing manufactured wood products, including engineered hardwood flooring, where movement due to shrinkage or expansion is minimized and dimensional stability is maximized.

Engineered hardwood flooring can be manufactured by drying a structural layer comprising a hardwood to a moisture content from about 0.1% to about 3%, whereupon a cell structure of the hardwood collapses. The dried structural layer can then be humidified to so that the hardwood has an increased moisture content greater than about 3%. A first outer layer can be coupled to a first side of the structural layer and a second outer layer can be coupled to a second side of the structural layer to form a three-ply product, where the structural layer is sandwiched by the first outer layer and the second outer layer. Coupling of the first outer layer and/or the second outer layer can effected using one or more adhesives or glues, or by using various fasteners or interlocking features between the various layers.

Methods of manufacturing engineered hardwood flooring are provided that include drying a structural layer comprising a hardwood to a moisture content from about 0.1% to about 3% so that a cell structure of the hardwood collapses. The dried structural layer is then humidified to where the hardwood has an increased moisture content from greater than about 3%. At least one coupling feature can be formed in the structural layer, the at least one coupling feature configured to allow the structural layer to be coupled to another structural layer. As one example, the at least one coupling feature can include tongue and groove features, where the tongue and groove are so dimensioned so that the tongue is received by the groove to form a substantially flush joint.

Various outer layers can be added to the structural layer. A first outer layer can be coupled to a first side of the structural layer, where the first outer layer can include a hardwood, a composite wood, a polymeric material, and combinations thereof. At least one coupling feature can be formed in one of the first outer layer and the structural layer, where the at least one coupling feature is configured to allow the one of the first outer layer and the structural layer structural layer to be coupled to another one of the first outer layer and the structural layer. A second outer layer can be coupled to a second side of the structural layer, where the structural layer is sandwiched by the first outer layer and the second outer layer. The first outer layer and the second outer layer can independently include a member selected from the group consisting of a hardwood, a composite wood, a polymeric material, and combinations thereof. At least one coupling feature can be formed in one of the first outer layer, the structural layer, and the second outer layer. The at least one coupling feature can be configured to allow the one of the first outer layer, the structural layer, and the second outer layer to be coupled to another one of the first outer layer, the structural layer, and the second outer layer. In certain embodiments, the engineered hardwood flooring consists essentially of a three-ply engineered product of the structural layer sandwiched by the first outer layer and the second outer layer and has complementary tongue and groove features.

An engineered hardwood flooring is provided that is made by methods provided herein. The engineered hardwood flooring can be made by drying a structural layer comprising a hardwood to a moisture content from about 0.1% to about 3%, whereupon a cell structure of the hardwood collapses, and humidifying the dried structural layer to where the hardwood has an increased moisture content greater than about 3%. The method of making can further comprise coupling a first outer layer to a first side of the structural layer. Similarly, a second outer layer can be coupled to a second side of the structural layer, the structural layer sandwiched by the first outer layer and the second outer layer. The first outer layer and the second outer layer can independently include a member selected from the group consisting of a hardwood, a composite wood, a polymeric material, and combinations thereof. At least one coupling feature can be formed in one of the first outer layer, the structural layer, and the second outer layer, where the at least one coupling feature configured to allow the one of the first outer layer, the structural layer, and the second outer layer to be coupled to another one of the first outer layer, the structural layer, and the second outer layer. Engineered hardwood floors are also provided, where such floors comprise the engineered hardwood flooring made according to the methods described herein.

Engineered hardwood flooring is provided that includes a structural layer comprising hardwood having a collapsed cell structure and a moisture content of greater than about 3%. The collapsed cell structure can be the result of super drying the hardwood to a moisture content from about 0.1% to about 3%. Engineered hardwood floors can be provided that include such engineered hardwood flooring. Methods of installing an engineered hardwood floor are provided that include placing a piece of engineered hardwood flooring as described herein on a floor and coupling thereto another piece of engineered hardwood flooring.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Figure 1:
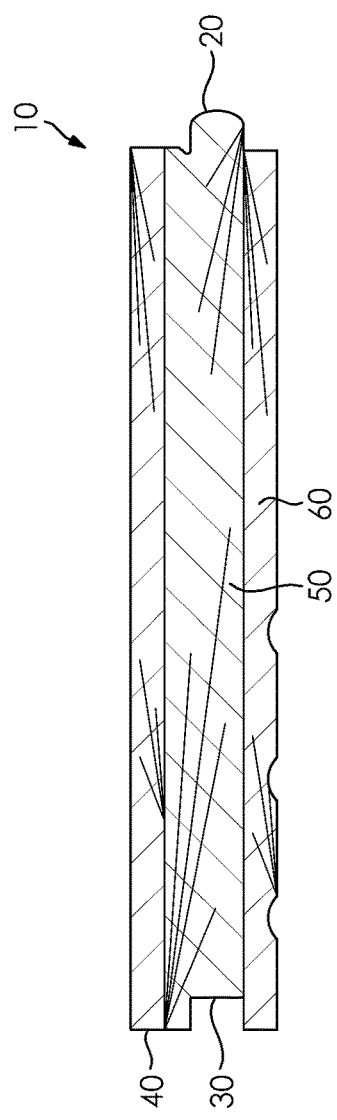
FIG. 1 depicts a cross section of a longitudinal end of a piece of three-ply engineered hardwood flooring constructed in accordance with the present technology.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments. "A" and "an" as used herein indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

All documents, including patents, patent applications, and scientific literature cited in this detailed description are incorporated herein by reference, unless otherwise expressly indicated. Where any conflict or ambiguity may exist between a document incorporated by reference and this detailed description, the present detailed description controls.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The present technology relates to the manufacture of engineered hardwood flooring. A structural layer comprising a hardwood is dried to a moisture content from 0.1% to 3%, whereupon a cell structure of the hardwood collapses. Having a moisture content from 0.1% to 3% is also referred to as a super-dried state. The dried structural layer is then humidified to increase the moisture content so that the moisture content is higher than the super-dried state. Humidification can therefore include where the hardwood has an increased moisture content greater than about 3%. For example, the structural layer can be dried to a moisture content of less than about 3% and then humidified to allow the moisture content to rise to greater than about 3%, where the humidification can increase the moisture content to between about 5% and about 6%. Humidification can continue to increase the moisture content to between greater than about 3% to about 20%. In some embodiments, the humidification increases the moisture content to between about 4% to about 12%.

A first outer layer can then be coupled or adhered to a first side of the structural layer and a second outer layer can then be coupled or adhered to a second side of the structural layer to form a three-ply product, the structural layer being sandwiched by the first outer layer and the second outer layer. Each of the first outer layer and the second outer layer can independently include another hardwood, a composite wood, a polymeric material, and combinations thereof. The three-ply engineered hardwood flooring can be configured to have one or more coupling features, such as a tongue-and-groove features, for assembly of multiple pieces of the flooring. Other types of coupling features can be used to join separate pieces of the engineered hardwood flooring, including one or more butt joints, lap joints, bride joints, dowel joints, mitre joints, finger joints, dovetail joints, mortise and tenon, cross lap, splice joints, biscuits, and combinations thereof. In this way, various widths of the flooring can be produced, where the three-ply flooring can provide pieces that do not shrink, expand, cup, etc. due to changes in the environment (e.g., humidity) as would be the case for solid hardwood flooring of equivalent widths.

Drying of the structural layer comprising the hardwood to a moisture content from 0.1% to 3% results in a "super dried" state for the hardwood. Several surprising and unexpected effects are attributable to this super-dried state. One particular effect is the collapse of wood cell structures, where it is hypothesized that the resulting collapse and/or increase in density is not reversible and/or makes the hardwood resistant to further collapse or shrinkage as well as any swelling or re-expansion. Humidification of the hardwood then increases the moisture content greater than about 3%. The structural layer including the hardwood treated in this manner minimizes any shrinkage/expansion movement in engineered flooring incorporating the same. For example, a piece of three-ply engineered hardwood flooring incorporating the super-dried hardwood in the structural layer shows reduced dimensional changes compared to a piece of three-ply engineered hardwood flooring where the hardwood in the structural layer was not super-dried. Reduction in dimensional changes is observed with respect to environmental humidity changes and/or environmental temperature changes.

In some embodiments, the hardwood of the structural layer can be dried and treated as follows. A kiln can be used to lower the moisture content of the hardwood to below about 3%. Moisture is then added back to the hardwood, raising the moisture content to greater than about 3%. For example, humidity within the kiln can be adjusted to raise the moisture content. It can also be possible to treat the super dried hardwood with steam to increase the moisture content. The moisture content can be deliberately increased to greater than about 3% by application of moisture (e.g., steam) and/or the natural hygroscopic nature of the hardwood can serve to increase the moisture content to greater than about 3% over time, where the super-dried structural layer can be left exposed to an environment having a relative humidity (RH) greater than about 3%. The hardwood can then be subjected to one or more additional conditioning processes to further remove inner stresses.

Treatment of the hardwood of the structural layer can also include a conditioning process as follows. Upon removal from the kiln, the hardwood is placed in a conditioning room where the air temperature is regulated at about 90° F. (32.2° C.) to about 100° F. (37.8° C.) and humidity is regulated at about 20% to about 25% RH. The hardwood of the structural layer is then coupled or adhered and sandwiched between outer layers within 72 hours of removal from the conditioning room, or returned to the conditioning room for a minimum of 12 hours for reconditioning. Coupling one or more outer layers to the structural layer can include adhering the respective layers using various glues or adhesives, or by using various fasteners or interlocking features between the various layers.

Various means can be used to ascertain the moisture content of the hardwood of the structural layer. These include the use of various moisture meters, such as commercially available moisture meters including those available from Wagner Meters (Rogue River, Oreg.) and Delmhorst Instrument Co. (Towaco, N.J.). Other ways to ascertain moisture content include various oven tests where a hardwood sample is weighed, placed in an oven to remove all water, and the sample is weighed again. The moisture content of a sample is ((weight of water) divided by (weight of wood))×100%, or put another way, the moisture content is (((initial weight of the sample) minus (oven-dried weight)) divided by (oven-dried weight))×100%. The oven can be held at about 217° F. (103° C.) and the sample can be dried in the ventilated oven until the weight is constant. Other oven test methods include those provided in the American Society for Testing and Materials publication ASTM D4442.

Embodiments of the present methods and engineered hardwood flooring formed thereby can further include the following aspects. The engineered hardwood flooring can join three layers of solid-sawn timber that are cross banded for balanced construction. One or both of the outer layers sandwiching the structural layer can be cut in different styles, including flat-sawn, quarter-sawn, and rift-sawn, where various cuts can give the outer surface(s) of the engineered hardwood flooring different final appearances. The layers can meld together and improve stability with far less expansion and contraction and without cupping. Moreover, only two coupling features, such as glue joints, need to be used, where the three layers can be fused in a microwave press that can ensure 100% adhesion the entire length of each piece of three-ply engineered hardwood flooring. Other types of presses can be used, such as a cold press. In certain embodiments, the engineered hardwood flooring consists essentially of a three-ply engineered product of the structural layer sandwiched by the first outer layer and the second outer layer and has complementary tongue and groove features. By "consists essentially of," it is mean that the three-ply engineered product of the structural layer sandwiched by the first outer layer and the second outer layer does not include any additional layers or coupling features beyond the complementary tongue and groove features that allow assembly of like pieces of the engineered hardwood flooring. Finally, all components can be processed with little or no byproduct waste and are environmentally friendly.

Engineered hardwood flooring made using the present technology can include the following parameters.

Product Construction: 3-ply platform of all hardwood solid sawn and cross plied for balanced construction.

Thickness: ¾" (19 mm) overall—to matches trims, vents and nosing's for easy installation. Custom thickness available.

Lengths: 18"-10' standard with 4'-5' average depending on grade. Custom averages and lengths to 12'.

Widths: 3"-9" and custom to 12" allow for a wide array of design options.

Wear layer: 3/16" (5 mm) standard, custom 4 mm and 6 mm available.

Milling: tongue and groove, end-matched, square edged, 0.010 tolerance ensures excellent fit and finish.

Species: most northern domestic and exotic woods, rift and quartered, herringbone available.

Grading: clear, select, natural XL and character standard. Custom grades and F.S.C. available.

Surface texture: true hand scraping, edge detailing, and wire brushing available. Pre sanding available.

Installation: nail or glue down according to N.W.F.A. guidelines.

Finish: standard unfinished square edge and pre-finished micro-bevel. Custom available.

Applications: radiant heat, concrete, plywood, oriented strand board, below grade, commercial and residential.

EXAMPLES

Example embodiments of the present technology are provided with reference to the figures enclosed herewith.

FIG. 1 depicts a cross section of a longitudinal end of a piece of three-ply engineered hardwood flooring 10 constructed in accordance with the present technology. Coupling features configured as tongue 20 and groove 30 features are included, where the tongue-and-groove, end-matched, square edged, and a 0.010 tolerance ensures excellent fit and finish between pieces of the engineered hardwood flooring 10. An outer layer 40, also known as a face layer or sawn wear layer, can be about 5 mm thick, where the outer layer 40 provides natural grain patterns indistinguishable from solid wood flooring and can be sanded and refinished. A structural layer 50 can be about 10 mm thick, where the example shown is a cross-banded American Cherry hardwood structural layer treated in accordance with the present technology to minimize movement and improve stability. Other types of hardwood can be used, such as silver maple and other cuts can be used. Another outer layer 60, also known as a bottom layer, is provided, where the structural layer 50 is sandwiched between the top outer layer 40 and the bottom outer layer 60. The bottom outer layer 60 can be a poplar base layer, for example. Other types of wood can also be used for the bottom outer layer 60, such silver maple, or other hardwoods.

Figure 2:
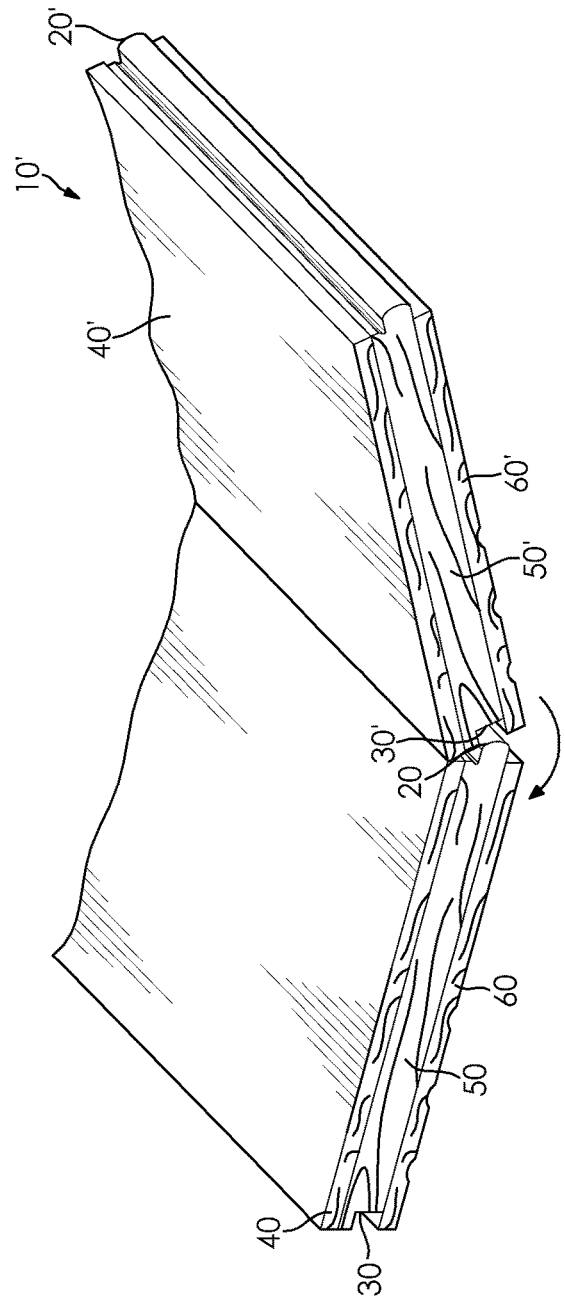
FIG. 2 is perspective view showing assembly of two pieces of the three-ply engineered hardwood flooring using tongue and groove features.

FIG. 2 is perspective view showing how two pieces of the three-ply engineered hardwood flooring 10 can be assembled together using the tongue 20 and groove 30 features. The piece of engineered hardwood flooring 10 from FIG. 1 is shown on the left side being coupled to another piece of engineered hardwood flooring 10' on the right side having similar features denoted using a prime symbol.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A method of manufacturing engineered hardwood flooring comprising:
   providing a first outer hardwood layer, an intermediate hardwood layer, and a second outer hardwood layer, the intermediate hardwood layer having a continuous structure between a first coupling end and a second coupling end of the intermediate hardwood layer, the first and second outer hardwood layers each having a flat inner surface extending between the first and second coupling ends of the intermediate hardwood layer;
   collapsing a cell structure of the intermediate hardwood layer by drying the intermediate hardwood layer to a moisture content from about 0.1% to about 3%;
   steam humidifying the dried intermediate hardwood layer to an increased moisture content of greater than about 3%; and
   coupling the first outer hardwood layer to a first side of the intermediate hardwood layer and the second outer hardwood layer to a second side of the intermediate hardwood layer, thereby forming a groove only in the intermediate hardwood layer and that is at least partially defined by the flat inner surface of the second outer hardwood layer, wherein the intermediate hardwood layer is sandwiched by the first outer hardwood layer and the second outer hardwood layer to form a protrusion, the protrusion is at the second coupling end of the intermediate hardwood layer, and the protrusion extends beyond the first and second outer hardwood layers.

2. The method of claim 1, wherein the second outer hardwood layer is a bottom outer layer, and further comprising providing at least one coupling feature formed by the bottom outer layer and the groove of the intermediate hardwood layer, the at least one coupling feature configured to allow the intermediate hardwood layer to be coupled to a protrusion of another intermediate hardwood layer.

3. The method of claim 1, further comprising providing at least one coupling feature that includes tongue and groove features.

4. The method of claim 1, further comprising providing at least one coupling feature configured to allow the groove to be coupled to a protrusion of another intermediate hardwood layer.

5. The method of claim 1, further comprising forming at least one coupling feature by at least one of the first and second outer hardwood layers and the intermediate hardwood layer, the at least one coupling feature configured to be coupled to another intermediate hardwood layer.

6. The method of claim 1, wherein the engineered hardwood flooring includes a three-ply engineered product comprised of the intermediate hardwood layer sandwiched by the first outer hardwood layer and the second outer hardwood layer, and the intermediate hardwood layer has complementary tongue and groove features.

7. The method of claim 1, wherein humidifying the dried intermediate hardwood layer includes subjecting the dried intermediate hardwood layer to a temperature between about 90° F. (32.2° C.) to about 100° F. (37.8° C.) and a humidity between about 20% to about 25% relative humidity.

8. The method of claim 1, wherein the intermediate hardwood layer is thicker than the first outer hardwood layer.

9. The method of claim 1, wherein the groove includes a lower groove, and the protrusion includes a lower protrusion.

10. A method of an engineered hardwood flooring, the method comprising:

providing a first outer hardwood layer, an intermediate hardwood layer, and a second outer hardwood layer, the intermediate hardwood layer having a continuous structure between a first coupling end and a second coupling end of the intermediate hardwood layer, the first and second outer hardwood layers each having a flat inner surface extending between the first and second coupling ends of the intermediate hardwood layer;

drying the intermediate hardwood layer to a moisture content from about 0.1% to about 3% such that a cell structure of the hardwood collapses;

humidifying the dried intermediate hardwood layer to an increased moisture content greater than about 3%;

coupling a first outer layer to a first side of the intermediate hardwood layer and a second outer layer to a second side of the intermediate hardwood layer, thereby forming a groove only in the intermediate hardwood layer and at least partially defined by the flat inner surface of the second outer hardwood layer, wherein the intermediate hardwood layer is sandwiched by the first outer hardwood layer and the second outer hardwood layer to form a protrusion at the second coupling end of the intermediate hardwood layer, and the protrusion extends beyond the first and second outer hardwood layers.

11. The method of claim 10, further comprising forming at least one coupling feature by at least one of the first and second outer hardwood layers and the intermediate hardwood layer, the at least one coupling feature configured to be coupled to another intermediate hardwood layer.

12. An engineered hardwood floor comprising the engineered hardwood flooring of claim 10.

13. The method of claim 10, wherein the groove includes a lower groove, and the protrusion includes a lower protrusion.

14. The method of claim 10, wherein humidifying the dried intermediate hardwood layer includes subjecting the dried intermediate hardwood layer to a temperature between about 90° F. (32.2° C.) to about 100° F. (37.8° C.) and a humidity between about 20% to about 25% relative humidity.

15. The method of claim 10, wherein the humidifying includes steam humidifying.

16. An engineered hardwood flooring comprising:
a first outer hardwood layer;
a second outer hardwood layer; and
an intermediate hardwood layer having a collapsed cell structure and a moisture content of greater than about 3%, wherein the intermediate hardwood layer has a continuous structure between a first coupling end and a second coupling end of the intermediate hardwood layer,
the first and second outer hardwood layers each having a flat inner surface extending between the first and second coupling ends of the intermediate hardwood layer,
the first outer hardwood layer being coupled to a first side of the intermediate hardwood layer, thereby forming a groove only in the intermediate hardwood layer and that is at least partially defined by the flat inner surface of the second outer hardwood layer, and
the second outer hardwood layer being coupled to a second side of the intermediate hardwood layer, wherein the intermediate hardwood layer is sandwiched by the first outer hardwood layer and the second outer hardwood layer, thereby forming a protrusion at the second coupling end of the intermediate hardwood layer, and the protrusion extends beyond the first and second outer hardwood layers.

17. An engineered hardwood floor comprising the engineered hardwood flooring of claim 16.

18. A method of installing an engineered hardwood floor comprising:

placing a piece of engineered hardwood flooring of claim 16 on a floor, and coupling thereto another piece of engineered hardwood flooring.

19. The engineered hardwood flooring of claim 16, wherein the groove includes a lower groove, and the protrusion includes a lower protrusion.

20. The engineered hardwood flooring of claim 16, wherein the protrusion is formed only of the intermediate hardwood layer.

* * * * *